United States Patent [19]

Fleischmann

[11] 4,186,751
[45] Feb. 5, 1980

[54] NON-INVASIVE, PRESSURE SENSOR APPARATUS FOR COMMUNICATING PRESSURE INSIDE A BODY TO THE EXTERIOR THEREOF

[75] Inventor: Lewis Fleischmann, Randallstown, Md.

[73] Assignee: Hittman Corporation, Columbia, Md.

[21] Appl. No.: 873,904

[22] Filed: Jan. 31, 1978

Related U.S. Application Data

[63] Continuation-in-part of Ser. No. 726,798, Sep. 27, 1976, abandoned.

[51] Int. Cl.$^2$ .............................................. A61B 5/00
[52] U.S. Cl. ...................................... 128/748; 73/729
[58] Field of Search .............. 128/2 P, 2.05 E, 350 V, 128/2 R, 748; 73/729

[56] References Cited

U.S. PATENT DOCUMENTS

| | | | |
|---|---|---|---|
| 3,187,181 | 6/1965 | Keller | 250/83 |
| 3,638,496 | 2/1972 | King | 73/398 R |
| 3,757,770 | 9/1973 | Brayshaw et al. | 128/2 R |
| 3,908,461 | 9/1975 | Turpen | 73/398 AR |
| 3,958,558 | 5/1976 | Dunphy | 128/2 P |
| 3,977,391 | 8/1976 | Fleischmann | 128/2 A |
| 4,006,735 | 2/1977 | Hittman et al. | 128/2 A |
| 4,014,319 | 3/1977 | Favre | 128/2 R |
| 4,022,190 | 5/1977 | Meyer | 128/2 A |
| 4,026,276 | 5/1977 | Chubbuck | 128/2.1 R |
| 4,027,661 | 6/1977 | Lyon et al. | 128/2 A |
| 4,062,354 | 12/1977 | Taylor et al. | 128/2 P X |
| 4,127,110 | 11/1978 | Bullara | 128/2 P |

OTHER PUBLICATIONS

Bustard et al., *A Nuclear Intra-Cranial Pressure Sensor*, IEEE Trans. on Nuc. Science, vol. 21, #1, Feb. 1974, pp. 697-701.

*Primary Examiner*—Robert W. Michell
*Assistant Examiner*—Francis J. Jaworski
*Attorney, Agent, or Firm*—Fleit & Jacobson

[57] ABSTRACT

A pressure sensor for indicating pressure in the animal or human body, such as intracranial pressure, including a housing, a bellows contained within the housing, a body pressure sensing tambour for placing the bellows in communication with pressure in the body so that the pressure will cause the bellows to move as a function of the pressure, output means, such as a radioactive source and associated shielding, contained within the housing and associated with the bellows for providing an output which is a function of the movement of the bellows, and a receiver, such as a radiation detector, located external to the body to receive the output and provide data indicative of the pressure in the body. The pressure sensor includes means associated with the bellows to enable in vivo calibration of the pressure sensor after implantation by establishing a preselected output condition during calibration. An ambient pressure sensing tambour is associated with the bellows for compensating for ambient pressure variations. The bellows is resilient, made of a material which has essentially 100% memory of position and has particular critical dimensions in order to provide linear movement in response to the range of pressures to be monitored, and to provide a sufficient movement, or deflection, in order to provide a sufficient readout. The bellows has a spring rate which is substantially greater than the spring rate of the pressure sensing and ambient pressure compensating tambours thereby making the pressure sensor essentially insensitive to temperature variations.

18 Claims, 8 Drawing Figures

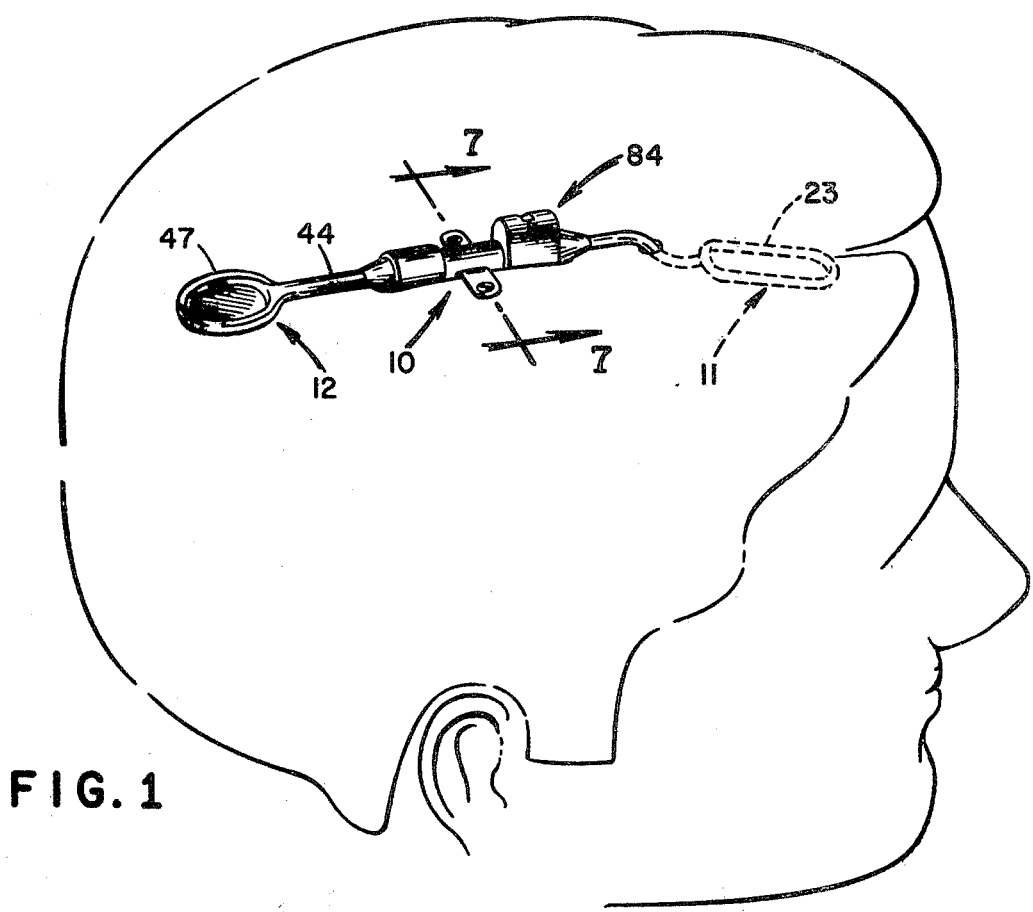
FIG. 1
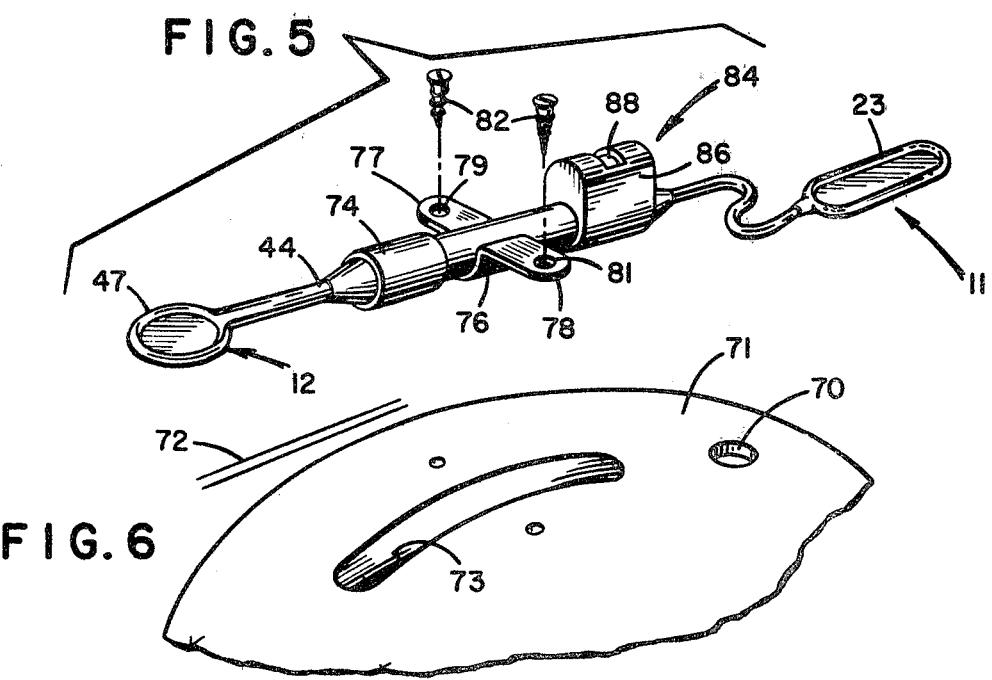
FIG. 5
FIG. 6

NON-INVASIVE, PRESSURE SENSOR APPARATUS FOR COMMUNICATING PRESSURE INSIDE A BODY TO THE EXTERIOR THEREOF

CROSS-REFERENCE TO RELATED APPLICATIONS

This application is a continuation-in-part application of Ser. No. 726,798, filed on Sept. 27, 1976, now abandoned.

This invention is related to commonly-assigned applications Ser. No. 488,988, filed July 16, 1974, for PRESSURE SENSOR, by Warren C. Lyon et al, now U.S. Pat. No. 4,027,661, and Ser. No. 592,718, filed July 3, 1975, for NON-INVASIVE NUCLEAR DEVICE FOR COMMUNICATING PRESSURE INSIDE A BODY TO THE EXTERIOR THEREOF, by Lewis Fleischmann et al, now U.S. Pat. No. 4,124,023.

BACKGROUND OF THE INVENTION

The need for a non-invasive technique for measuring the pressure in body cavities of animals or humans is recognized as highly desirable for continuous or intermittent monitoring of body conditions. Such cavities as the cranium, vena cava, bladder, and others provide valuable and sometimes critical information for maintaining the well being or survival of an animal or human. For example, it is known that intracranial pressure provides a valuable indication of well being for a variety of clinical conditions, including shock trauma and hydrocephalus.

Accordingly, there is a recognized need for a pressure sensor for continuous or intermittent monitoring of body conditions. In particular, there is a need for a pressure sensor having compensation for ambient pressure variations and low sensitivity to temperature changes. Moreover, there is a need for a sensor which can be calibrated in vivo and which provides an output which accurately reflects the pressure in the animal or human body.

SUMMARY OF THE INVENTION

The pressure sensor of the present invention is fully implantable and contains output means, such as a radioactive source and associated shielding, so that the pressure can be readout non-invasively. In its preferred form, the pressure sensor includes a housing containing a bellows in communication with a body pressure sensing tambour placed in the body and exposed to the pressure to be sensed. An ambient pressure sensing tambour is also associated with the bellows for compensating for ambient pressure variations. The housing is located external to the cavity being sensed and preferably situated just under the skin. The housing also contains the output means, which is associated with the bellows.

The pressure acting upon the body pressure sensing tambour causes the bellows to expand and contract. The movement of the bellows causes the output means to provide an output, which is a function of the pressure such as by causing radiation shielding to shield a radioactive source as a function of the pressure sensed. The output is sensed from outside the body by a receiver, such as a conventional nuclear counter or crystal detector instrument in case of a radiation output.

The pressure sensor also includes means associated with the bellows to enable in vivo calibration of the pressure sensor after implantation by establishing a preselected output condition during calibration. More specifically, and using a radioactive source and associated radiation shielding as illustrative, a stop is provided so that there is a preselected radiation output which can be used for calibration.

The bellows is resilient, made of a material which has essentially 100% memory of position, and has particular critical dimensions in order to provide a linear movement, or deflection, in response to the complete range of pressures to be monitored, and to provide a sufficient movement in order to provide a sufficient readout. The bellows has a spring constant substantially greater than the spring constant of the body and ambient pressure sensing tambours, which offer effectively no resistance to pressure changes, thereby making the pressure sensor essentially insensitive to temperature variations.

The pressure sensor is fully implantable and does not require any energy source other than the radioactive material, for example, contained in the device. Another major advantage of the sensor is the elimination of leads or other penetrations through the skin to provide power or transmit a signal. With a long-lived radiosotope, such as promethium-145, carbon-14, nickel-63, strontium-90, or americium-241, the inventive pressure sensor can be fully implanted and left in place for the life of the patient.

The pressure sensor functions accurately to within several millimeters of water pressure and is unaffected by variations in ambient pressure. Also, it is generally insensitive to ambient temperature and can be calibrated in vivo. Furthermore, the materials used to construct the sensor are biologically inert and do not pose any health hazard to the animal, or human body, or make the patient more susceptible to mechanical trauma. The sensor unit is of relatively small size and so does not produce unsightly bulging when implanted subdermally.

Other features and advantages of the invention will be apparent from the following description of the preferred embodiments of the invention as shown in the accompanying drawings.

BRIEF DESCRIPTION OF THE DRAWINGS

FIG. 1 is a perspective view of a preferred embodiment of the non-invasive pressure sensor of the invention in an installed position for monitoring the pressure in an intracranial cavity and communicating the monitored pressure to the exterior of the body;

FIG. 2 is a plan view of the apparatus of FIG. 1;

FIG. 3 is a sectional view taken substantially along line 3—3 of FIG. 3 in the direction of the arrows;

FIG. 4 is an enlarged sectional view of a portion of the apparatus of FIG. 3;

FIG. 5 is an enlarged perspective view of the mounting arrangement for the apparatus of FIG. 1;

FIG. 6 is a perspective view of a portion of the skull of a patient prior to installation of the apparatus of the invention;

DESCRIPTION OF THE PREFERRED EMBODIMENTS

Figure 7:
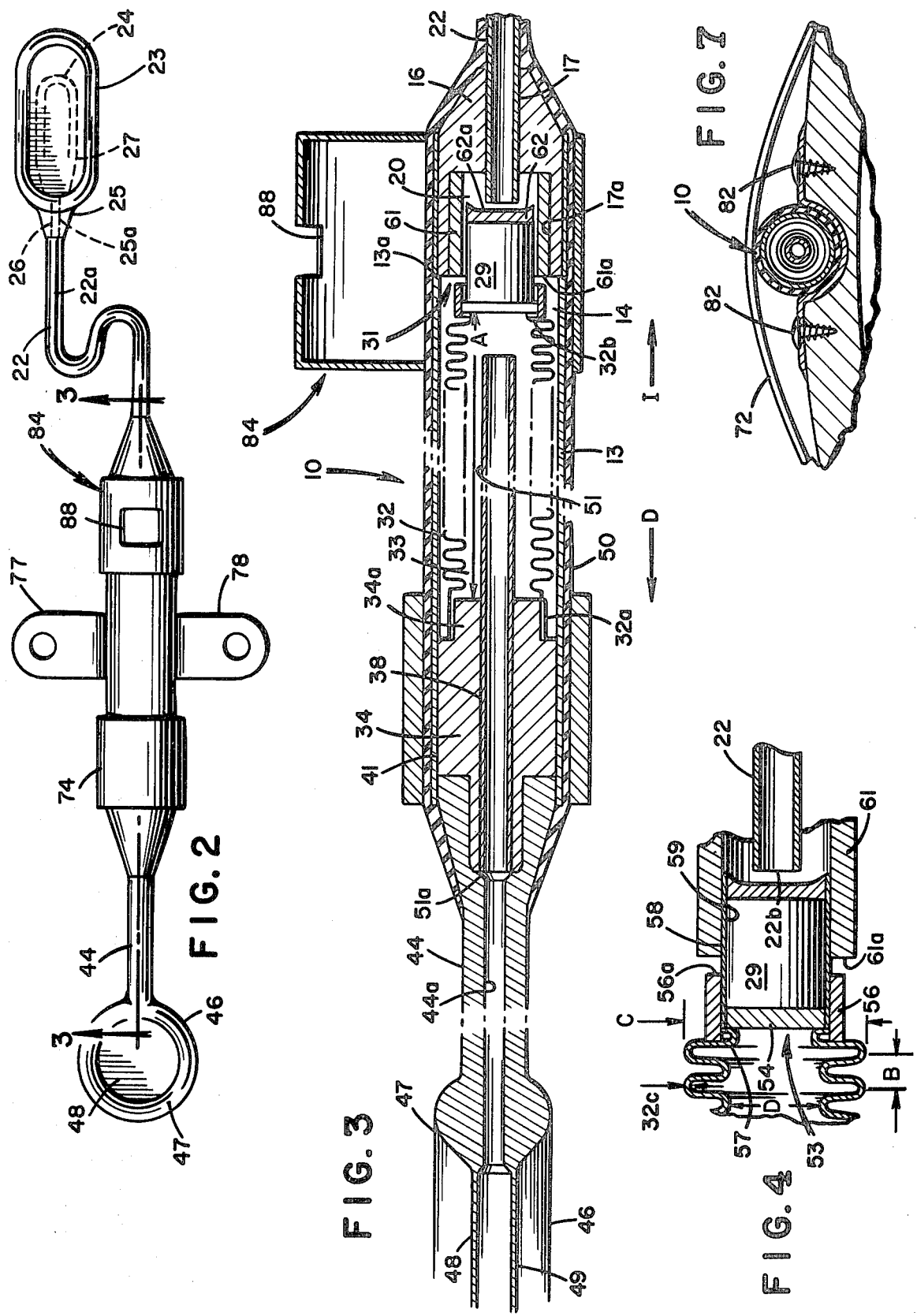
FIG. 7 is a sectional view taken substantially along lines 7—7 of FIG. 5 in the direction of the arrows.

Referring now to the drawings and to FIGS. 1 and 2 in particular, there is shown the pressure sensor apparatus of the invention with a housing designated generally by the numeral 10, and a body pressure sensing means designated generally by the numeral 11 and connected to the housing 10 for sensing the pressure in a body portion, such as a cavity. Ambient pressure sensing means, designated generally by the numeral 12, is also connected to the housing 10, and is responsive to ambient pressure to compensate for changes in ambient pressure during the operation of the apparatus. Although the pressure sensor apparatus of the invention is shown in an installed position on the head of a human body for non-invasively monitoring intracranial cavity pressure and communicating it to the exterior, it should be understood that this is only a preferred example of the invention and that it is equally adaptable for monitoring pressure in other areas of the body, both animal and human. Therefore, while the description to follow will be directed to the use of the invention for monitoring intracranial cavity pressure, it should be understood that the invention is equally applicable to monitoring pressure in other body portions and cavities.

Referring now to FIG. 3, and as specifically illustrative of the invention, the housing 10, which is preferably formed of titanium, is of tubular shape having a side wall 13 defining an interior 14. A first support member 16, also preferably formed of titanium, has a central bore 17 positioned within one end of the housing 10 in sealing relationship with the housing side wall 13 by means of an epoxy resin or the like. Preferably, an annular shoulder 13a is formed in the housing side wall 13 for positioning the support member 16 in a precise location within the housing 10, as will be explained hereinafter. The first support member central bore 17 is provided with a portion 17a of substantially enlarged diameter defining a recess 20 which communicates with the interior 14 of the housing 10.

The body pressure sensing means 11 includes a fluid conduit 22 of deformable metallic material, preferably titanium, which has been heat treated for formability, one end 22a of which is arranged to be connected to the body pressure sensing device or tambour 23 having an interior 24, which is arranged to be positioned within a body cavity, such as the intracranial cavity of FIG. 1.

The tambour 23 is formed of a suitable elastomeric material, such as medical grade Silastic rubber and is of a substantially flat configuration including a neck portion 25 in the wall of which is molded a helical spring 26, preferably of stainless steel, for imparting rigidity to the neck portion 25. The neck portion 25 includes a central bore 25a which communicates with the interior 24 of the tambour 23, and which is arranged to receive the end 22a of the conduit 22, as shown in FIG. 2. Preferably, a U-shaped clip 27 of tantalum or the like is disposed within the interior 24 of the tambour 23 for maintaining the side walls of the tambour in spaced-apart relationship, and to serve as a locating means for the tambour with the use of X-rays. The tambour 23, the fluid conduit 22 and the communicating portions of the housing interior 14, including the recess 20, are filled with a pressure transmitting fluid through which the pressure sensed by the tambour 23 in the body cavity is transmitted to the housing interior 14.

The conduit 22 is press-fitted through the bore 17 with the end 22b of the conduit 22 extending through the bore 17 into the recess 20, as shown best in FIGS. 3 and 4. Sealing engagement between the conduit 22 and bore 17 is obtained by means of epoxy resin or the like. Thus, the conduit end 22b communicates with the recess 20 and with the housing interior 14.

The output means of the pressure sensor apparatus preferably comprises a source 29 of radioactive material, normally in the form of a shaped article, disposed within the housing interior 14 together with associated radiation shielding means designated generally by the numeral 31. Means are provided in the housing interior 14 for resiliently urging the radioactive material and radiation shielding into a shielding relationship. More specifically, resilient means, such as a bellows 32, having an interior 33 is disposed within the housing interior 14, one end 32a of which is mounted on a necked-down portion 34a of a second support member 34, preferably formed of titanium, suitably mounted in the other end of the housing 10 in sealing engagement with the housing side wall 13 by means of an epoxy resin or the like. The other end 32b of the bellows 32 is closed, as will be explained hereinafter.

The second support member 34 is provided with a central bore 38 and the neck-down portion 34a is arranged to support the bellows end 32a in a sealing relationship therewith by means of an epoxy resin 41 or the like.

In the design of a system for intracranial pressure measurement that is to be implanted in the body, the most apparent design constraint relates to the size of the sensor. Quite obviously, the device must be of a size and configuration that is capable of being positioned in the human head as unobtrusively as possible. Further, the bellows 32 must not only be of a size and shape capable of being accommodated within the human body, but must also have characteristics capable of expansion and contraction in a manner to efficiently cause communication of its movement to a remote sensor. Thus, the bellows must be sensitive to the complete range of intracranial pressures that are to be sensed, such pressures typically being between 0 and 100 centimeters of water, in order to move a predetermined distance depending upon the sensitivity of the device to obtain an accurate readout. The bellows must be sensitive enough to give a complete range of movement, and thus a complete range of pressure readouts. In addition, the bellows 32 should be linearly responsive to negative pressure, for calibration purposes, over a pressure range of 0 to minus 35 centimeters of water.

In order to accurately monitor the pressure within the human body, it is necessary that the deflection, or movement, of the bellows be linear over the entire pressure range to be monitored. If the deflection is not linear, then the sensor that detects the radioactivity requires complex electronic circuitry that is quite expensive and, moreover, relatively inaccurate. It is, quite simply, much easier and much more accurate to detect linear motion rather than curvilinear or higher order pressure responses.

Thus, it is essential that the deflection of the bellows 32 be as linear as possible over the entire pressure range that the device is to monitor. Moreover, since the preferred embodiment of this invention requires monitoring of human body pressure by means of relative movement between a radioactive source 29 affixed to the bellows 32 and a shield 31, the deflection, or movement, of the bellows must be substantial enough that measurable reading changes are obtained. That is, it is essential that the deflection must be fairly substantial and linear in order for the device to achieve its desired results.

It has been determined that, in order to monitor pressure over a range of 0 to 100 centimeters of water, the deflection, or movement, of the bellows 32 must be in the order of 0.035 inches (35 mils), in order to obtain accurate measurements. Of course, due to the small size of the bellows 32, and the inherent difficulties encountered in the manufacture of such a small bellows, the dimensions to be discussed below, deflections of the bellows up to plus or minus 30% can be tolerated. Thus, the critical range of the bellows 32 deflection is between 0.0245 inches (24.5 mils) and 0.0455 inches (45.5 mils), given the size of the bellows discussed below.

As shown in FIG. 3, the bellows 32 is substantially cylindrical in shape and is convoluted over its entire workable length. The workable length A, as shown in FIG. 3, is the length of the bellows 32 between the necked-down portion 34a of the second support member 34 and an annular side member 56, described below. In its at-rest condition, the length A of the bellows is 0.410 inches (410 mils), and has 41 convolutions over this length. Thus, each convolution has a pitch, or cycle, B of 0.010 inches, as shown in FIG. 4.

The thickness 32c of the bellows 32 ranges from 0.00025 to 0.00033 inches (0.25 to 0.33 mils). The outer diameter C of the convoluted bellows 32 is 0.100 inch (100 mils) and the inner diameter D is 0.060 inch (60 mils). Thus, the mean cross-sectional area of the convoluted bellows 32, derived from the formula A mean $=\pi/2(\overline{O.D.}^2-I.D.^2/2)$, thus equals 0.005 in$^2$.

The bellows 32 is made of a resilient material having an essentially 100% memory of position. The bellows 32 is a gold-plated nickel bellows and is manufactured in the following manner. First, an aluminum mandrel is machined having the overall general shape of the bellows. The mandrel is then dipped in nickel bath and is electroplated. Following the nickel bath electroplating, it is dipped in a copper bath for a very thin copper layer to be applied thereover. The copper layer provides for leaktight integrity. Thereafter, the copper layer is plated once more with a nickel bath. Following the nickel plating, a layer of gold plating is electroplated thereon. Gold plating is necessary, since gold is chemically inert, and will not react with the saline in the body. Following the nickel and gold plating, the mandrel is dipped into a sodium hydroxide solution, and the aluminum mandrel is dissolved.

It should be noted that the manufacture of the bellows 32 having the particular dimensions and material discussed above will result in a bellows 32 having a spring rate of 0.186 lbs/inch. However, in the manufacture of such thin-walled bellows using the electroplating technique discussed above, manufacturing difficulties naturally arise. For example, in plating such thin-walled bellows, it is difficult to maintain the bellows wall sufficiently and uniformly thin. This is due to many factors, one of which is that the distances between the electrodes and the mandrel vary depending upon the orientation of the mandrel relative to the electrodes. Thus, due to the manufacturing factors, it has been found that the spring rate can vary plus or minus 30%, and even for a single bellows, the spring rate will vary slightly depending upon the pressure.

Thus, while the optimum spring rate is 0.186 lbs/inch, and should theoretically occur, given the particular size of the bellows disclosed above, manufacturing difficulties inherent in such thin-walled bellows manufacture may result in a variance from this optimum level. It has been determined that an average spring rate varying between 0.130 lbs/inch and 0.242 lbs/inch can satisfactorily perform the desired linear movement over the full range of pressures to be sensed. This average spring rate is determined in the following manner. First, a bellows is tested by applying a 1 gram weight thereto, and then measuring the deflection. The spring rate can then be calculated. Next, a 2 gram weight is applied to the bellows, the deflection measured, and the spring rate calculated. The average spring rate is then determined by calculating the average of the two spring rates taken with the different weights. This average spring rate must be within the range of 0.130 lbs/inch to 0.242 lbs/inch.

Figure 8:
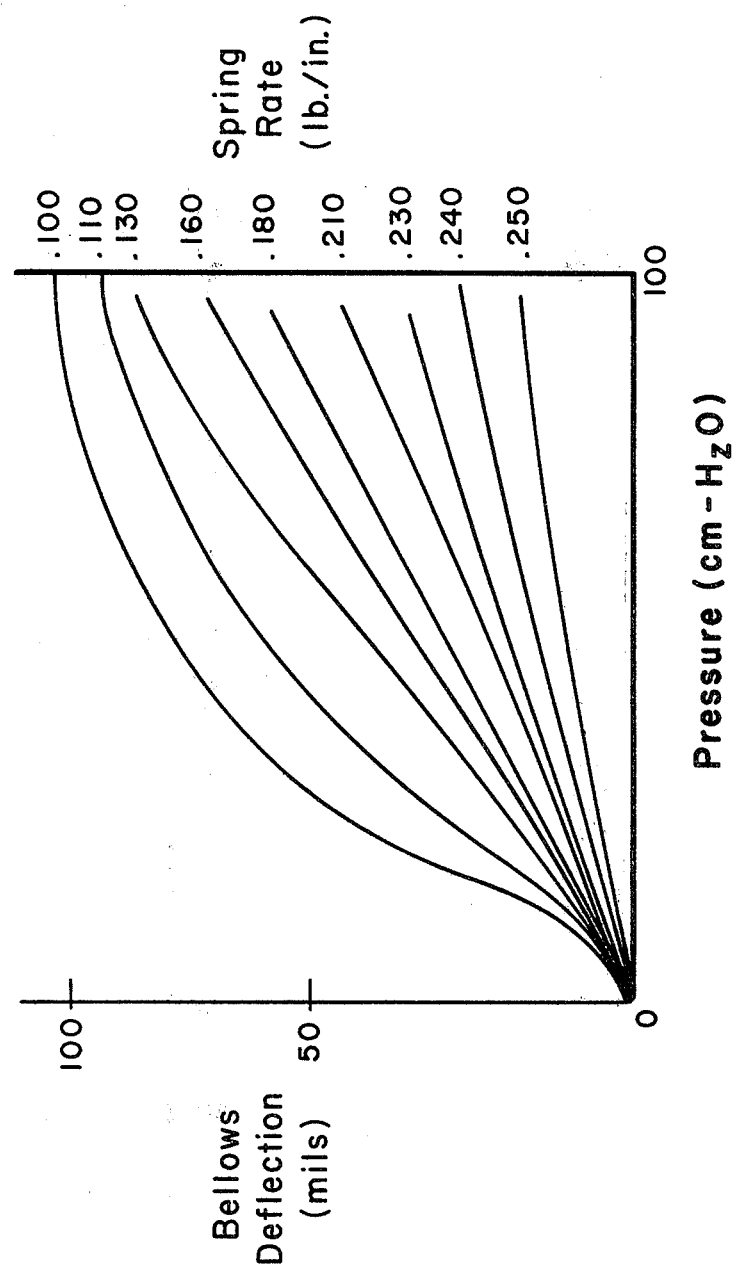
FIG. 8 is a graph of the bellows deflection versus pressure for a number of bellows of differing spring constants.

It has been discovered that there is a critical range for the spring constant to obtain optimum utilization of the pressure sensor given the particular dimensions of the bellows and the particular function of the bellows. Above this critical spring constant, the bellows becomes too insensitive for proper functioning. Below this critical spring constant, the bellows not only has manufacturing irregularities, discussed above, but does not provide a linear output of the bellows movement in response to pressure over the range to be monitored. In FIG. 8, a chart is shown plotting the bellows deflection, in response to pressure changes for a number of different bellows having different spring constants. It can be seen that the deflection in mils of a bellows having an average spring rate below 0.130 pounds per inch is essentially S-curved and substantially nonlinear over the entire range of pressures to be sensed. In order to accurately monitor such nonlinear movement, elaborate and complex electronic circuitry is required. Generally, the electronic circuitry to monitor such curvilinear movement requires a device that approximates the curve by considering the tangents to the curve. It is most desirable, from a design standpoint and from an accuracy standpoint, to have the movement of the bellows be as linear as possible. Thus, as can be seen from FIG. 8, the bellows deflection is substantially linear over the range of pressures to be monitored when the average spring rate is greater than 0.130.

However, as FIG. 8 makes clear, if the spring rate becomes too high, the sensitivity of the bellows decreases. Thus, it can be seen that for an average spring rate of 0.250 pounds per inch, although the curve is relatively linear, the deflection of the bellows for slight pressure changes may be too minimal for detection, especially when using a nuclear source-shield communication system. Thus, it has been determined that average spring rates greater than 0.242 pounds per inch are undesirable.

The central bore 38 of the second support member 34 includes a portion of enlarged diameter forming a recess 42 and which is provided with an annular, inwardly directed flange 43. The recess 42 receives the nipple 44 having a central passage 44a of an ambient pressure sensor or tambour 46 forming the ambient pressure compensating means 12. The tambour 46 is formed of a flexible material, preferably an elastomeric material, such as medical grade Silastic rubber, and includes an annular peripheral portion 47 and a recessed central portion 48 defining an interior 49 extending through the nipple central passage 44a.

A suitable adheseive, such as a medical Silastic adhesive, seals the nipple 44 in the recess 42 and the annular flange 43 compresses the outer surface of the nipple 44 to form a mechanical compression seal to securely retain the nipple 44 in the recess 42.

A rigid metal tube 51, preferably formed of titanium, is also sealed in nipple 44, such as by a Silastic adhesive, and extends through nipple central passage 44a and the central bore 38 of the second support member 34 into the bellows interior 33 to communicate the interior 49 of the tambour 46 with the bellows 32. The other end 51b of the tube 51 forms a stop for the bellows end 32b.

In order to transmit the sensed ambient pressure to the interior of the bellows 32, the interior of tambour 46, the bellows interior 33 and the tube 51 are filled with a pressure transmitting fluid, isolated by means of the bellows 32 from the pressure transmitting fluid in the body pressure sensing means 11. In the preferred embodiment, all of the exposed metallic surfaces of the sensing apparatus of the invention are coated with a suitable biocompatible material, such as a medical grade Silastic adhesive. As shown in the drawings, this Silastic adhesive 50 extends from the nipple 44 of tambour 46 to the joint between the metal conduit 22 and the neck portion 25 of tambour 23.

In the illustrated embodiment, the radiation shielding means 31 includes a first portion 53 of radiation shielding material such as tantalum having a cup-shaped configuration. The first portion 53 preferably includes an end plate 54, typically in the form of a disc, and an annular side member 56 both mounted on the other end 32b of the bellows 32 in closing relationship therewith, as shown in FIG. 4.

The radiation shielding means first portion 53 is mounted on an inwardly directed channel portion 57 adjacent the last accordion pleat in the bellows 32, and a tubular sleeve portion 58 extends axially outward therefrom which together define an enclosure 59. The end plate 54 is adhesively secured in the end of the enclosure by a suitable adhesive, such as an epoxy resin closing the end 32b of the bellows 32. Similarly, side member 56 is adhesively secured by means of an epoxy resin to sleeve portion 58.

The radiation shielding means also includes a second portion 61 in the form of a tubular sleeve of radiation shielding material, also preferably made of tantalum, which is press-fitted or the like within the recess 20 of the first support member 16. It can be seen that the second portion 61 extends throughout the depth of the recess 20 and has a forward end edge portion 61a terminating flush with the end of the first support member 16 abutting the housing side wall shoulder 13a. Thus, the second portion end 61a is precisely positioned axially in the housing interior 14 adjacent the end edge portion 56a of the first portion side member 56.

Radioactive source 29 is mounted on the end 32b of the bellows 32 and is accommodated for guiding movement within the radiation shield means second portion 61 disposed in the recess 20. As will be appreciated, however, the radiation shielding means, rather than the radioactive source 29, may be mounted on bellows 32, such an arrangement merely representing an obvious reversal of cooperating parts. The radioactive source 29, which is preferably of cylindrical shape, has an outer diameter conforming generally to the inner diameter of the bellows sleeve portion 58, and is adhesively secured within the enclosure 59 defined by the tubular sleeve portion 58 by means of a suitable adhesive, such as an epoxy resin. The end cap 62 has a meniscus 62a formed by the adhesive material.

The bellows 32 resiliently urges the radioactive source 29, together with the sleeve portion 58, in the direction of the arrow I into the recess 20 with the edge portion 56a of the radiation shielding means first portion side member 56 in adjacent cooperating relationship with the edge portion 61a of the tubular sleeve forming the radiation shield means second portion 61 to establish a shielding relationship with the radioactive source 29. The end cap 62 is, therefore, disposed adjacent the outlet end 22b of the pressure transmitting fluid conduit 22, as will be discussed in more detail hereinafter.

The outer diameter of the bellows sleeve portion 58 is selected to produce a loose-fitting relationship with the inner surface of the sleeve forming the radiation shielding means second portion 61, so that fluid introduced into the recess 20 from the end 22b of the conduit 22 may flow freely therebetween and through a gap between the first and second end edge portions 56a and 61a, respectively, to fill the interior 14 of the housing 10 on the outside of the bellows 32.

It should be understood that in the assembled apparatus of the invention before installation in the body, there is virtually no pressure differential in the housing 10 between the pressure-transmitting fluids on opposite sides of the bellows 32. In this condition, there is a gap, as will be discussed in more detail hereinafter, between the adjacent end portions 56a and 61a of the first and second portions 53 and 61, respectively. When the apparatus is installed in the body, the normal fluid pressure in the body cavity slightly increases the pressure on the tambour 23 introducing additional pressure transmitting fluid into the housing interior 14 on the outside of bellows 32, moving the bellows in the direction of the arrow D, and thereby increasing slightly the gap between the end edge portions 56a and 61a.

In the operation of the invention after installation, an increase in body pressure is sensed in the body cavity by the body pressure sensing device or tambour 23, the sensed pressure is transmitted by the pressure transmitting fluid flowing into the support member recess 20 through the end 22b of conduit 22 around the end cap 62 through the gap between the edge portions 56a, 61a to move the bellows 32 together with the radiation shielding means first portion 53, and the radioactive source 29 in the direction indicated by the arrow D in opposition to the urging force exerted by the bellows. During this movement, the radiation shielding means first and second portions 53, 61 move apart increasing the gap proportionally with the increase in cavity pressure thereby modifying the shield relationship between the shielding means 31 and radioactive source 29 to expose more of the radioactive source in accordance with the magnitude of the cavity pressure. The radioactive output of the exposed portion of the radioactive source 29 may then be sensed by a receiver means (not shown), such as a conventional nuclear counter or crystal detector disposed externally of the housing 10 and the body.

The provision of the ambient pressure sensing means 12 permits the pressure sensor apparatus of the invention to be responsive to pressure changes in the body cavity regardless of ambient pressure changes. More specifically, ambient pressure changes are imposed equally on both the ambient pressure sensing means 12 and body pressure sensing means 11, whereby the sensing apparatus of the invention responds to body cavity pressure changes only.

The pressure sensor apparatus of the present invention is essentially insensitive to ambient temperature variations, as well as temperature variations, which may occur inside the animal or human body whose pressure is being monitored. More specifically, bellows 32 has a spring constant, which is orders of magnitude greater than the spring constant of pressure sensing tambours 23 and 46, which offer effectively no resistance to pressure changes. Accordingly, any volumetric changes in the pressure transmitting fluid due to temperature variations in the body, or ambient temperature changes, will act to distend the body pressure sensing tambour 23 and ambient pressure sensing tambour 46, respectively, instead of causing a somewhat (contraction or expansion) of bellows 32. Therefore, temperature variations, whether external or internal to the cavity being monitored, do not affect or change the output of the pressure sensor apparatus and, therefore, do not cause erroneous pressure measurements.

A unique feature of the present invention is the provision of means to enable in vivo calibration of the pressure sensor apparatus after implantation by establishing a preselected output condition during calibration. More specifically, in accordance with the present design, and using a radioactive source and associated radiation shielding as illustrative, a stop is provided so that there is a preselected radiation output during calibration. This stop is provided in the embodiment illustrated by the end 22b of fluid conduit 22. After the pressure sensor apparatus is implanted, the surgeon can calibrate the instrument by pressing on the ambient pressure compensating tambour 46, which will cause the pressure transmitting fluid in the interior of tambour 46, the bellows interior 33 and the tube 51 to move bellows 32 and radioactive source 29 in the direction of arrow I, so that the end cap 62 abuts against the end 22b of conduit 22. In this extreme stop position, there is a fixed and repeatable amount of radiation emitted from the pressure sensor apparatus.

Because the housing 10, in which the output means of the pressure sensor apparatus is housed, is implanted under the scalp, for example, the scalp or other body tissue surrounding the housing will attenuate the radiation output signal as a function of the scalp thickness. Accordingly, in the laboratory before implantation, the radiation output from the pressure sensor apparatus with bellows 32 and radioactive source 29 at the extreme stop position is measured for a range of simulated scalp thickness, for example, 3 millimeter, 6 millimeter, and 9 millimeter of simulated scalp thickness. This measurement is also made over a range of pressures which corresponds to the pressures, which would normally be encountered in the particular body cavity being monitored. Then, a family of curves is produced, which correlate the radiation output with the pressure being monitored for each scalp thickness. After the sensor is implanted, the surgeon performs the in vivo calibration, as described above by pressing on the ambient pressure compensating tambour 46 and forming bellows 32 and radioactive source 29 to the extreme stop position. The radiation count obtained will fall on or near one of the family of curves. This curve is then used in monitoring the pressure.

To ensure a long life for the pressure sensing apparatus of the invention commensurate with body compatibility, it has been found that specific nonreactive fluids and elastomeric meterials eliminate such reactions. More specifically, the best results that have been obtained are when the elastomeric material of the various components are formed, in one example, from a Silastic type of silicone rubber, and the pressure-transmitting fluids are either castor oil or mineral oil between which there is virtually no chemical or physical reaction, thereby ensuring proper functioning of the pressure sensor apparatus throughout its life. It has also been found that, when the pressure-transmitting fluid is a silicone oil, the outstanding results of the invention are accomplished when the elastomeric materials are selected from the group consisting of butyl, neoprene, Buna N and Viton A rubbers. It should be understood, however, that other elastomeric materials and fluids perform satisfactorily but with less desirable results.

One major concern in selecting a fluid is the osmotic pressure effects produced during implantation. In order to eliminate these effects, it is preferred that a simulated cerebrospinal fluid be used as the pressure-transmitting medium and it may be used with all materials of construction, as it will be compatible with body fluids, and will not leak through the elastomeric materials, as a consequence of osmotic pressure.

In the use of the invention to monitor the fluid pressure within an intracranial cavity and with reference to FIGS. 5-7, the common practice is to provide a burr hole or aperture 70 within the bony structure of skull 71 overlying the intracranial cavity, through which the metallic fluid conduit 22 is inserted, the body pressure sensing device 23 being suitably disposed within the intracranial cavity. A body pressure sensing means, such as tambour 23, is normally positioned subdurally. However, it should be appreciated that the invention also contemplates positioning the body pressure sensing means 11 epidurally, in which case the shape and size of the tambour will be appropriately changed. The housing 10, together with the ambient pressure compensating device 12, are mounted on the outer surface of the skull 71 under the scalp 72.

The apparatus of the invention includes means for permanently mounting the housing 10 and ambient pressure sensing means 12 subcutaneously on the outer surface of the skull 71 in an inconspicuous, securely retained position. More specifically, an elongated concave groove 73 is formed within the outer surface of the skull 71 adjacent the burr hole 70, and mounting means are provided for securing the housing 10 in a seated relationship within the groove 73. The mounting means includes at least one, preferably two, tabs 74 arranged in longitudinally spaced relationship on the housing 10, as shown best in FIG. 5. Each of the tabs 74 includes an intermediate portion 75 of arcuate cross-sectional shape for accommodating the tubular housing 10 in underlying engagement therewith. The tab portion 76 is secured to the outer surface of the housing 10 by suitable means, such as a body compatible adhesive, welding or the like. The tabs 74 also include oppositely disposed end portions 77 and 78 extending laterally outward of the housing 10 secured within the intermediate portion 76.

Openings 79, 81 are provided in the tab end portions 77, 78 respectively for accommodating screw means, such as screws 82 extending therethrough in threaded engagement with the underlying bone of the skull 71, and with the end portions 77, 78 in overlying engagement with the outer surface of the skull 71, the tab intermediate portion 76 and housing 10 being accommodated within the groove 73.

In the preferred embodiment, the tabs 74 are preferably formed of a radiation shielding material, such as tantalum. One of the tabs 74 is positioned on the housing 10 with its intermediate portion 76 extending throughout the path of movement of the radioactive source 61 within the housing. Thus, not only does the one tab 74 prevent downwardly directed radiation into the body, but the radioactive output of source 29 is confined in a nonattenuating manner to the upward direction to permit easy detection by an externally positioned detection device.

The output of the radioactive source 29 needs only be of an extremely low order of magnitude, typically less than 10.0 microcurie, a magnitude far less than that at which the adjacent body tissue may be adversely affected. However, it should be characterized by an extremely precise and uniform output rate, which accurately reflects the changes in fluid pressure within the body cavity throughout its range of operation. The preferred radioisotopes used in the present invention are promethium-145, carbon-14, nickel-63, strontium-90 and americium-241 and, to obtain the proper radioactive output from the source 29, it should be in the form of a shaped article of highly homogeneous composition.

The radioactive source 29 typically comprises promethium chloride ($PmCl_3$), for example, uniformly distributed and absorbed onto an inert carrier, such as diatomaceous earth and uniformly distributed throughout a suitable binder, such as an epoxy resin. Sources 29 of this composition are extremely uniform regarding the concentration or distribution of the radioisotope.

Although the invention has been described in terms of a single preferred embodiment, nevertheless, changes and modifications may be made within the scope of the invention. For example, the pressure sensor apparatus, as illustrated, provides an output which is a direct function of the pressure being monitored, since the output increases with increasing body cavity pressure. However, as will be appreciated by one of ordinary skill in the art, the sensor can also be constructed so that the output is an indirect function of the pressure by mounting the radioactive source and the associated radiation shielding, so that the radioactive source is increasingly shielded by the radiation shielding, as the pressure being monitored increases. In this type of arrangement, the in vivo calibration is performed in the same manner as described herein except that the output will be a predetermined maximum output, rather than a predetermined minimum output. Accordingly, the invention should not be limited by the specific embodiment illustrated but only as defined in the appended claims.

I claim:

1. A pressure sensor apparatus for indicating pressure in the body comprising a housing, a gold-plated nickel bellows contained within said housing, said bellows having a plurality of convolutions and a length over the convoluted portion of substantially 0.410 inch, a wall thickness substantially within the range of 0.00025 to 0.00033 inch, and an average spring rate of substantially 0.130 to 0.242 pounds per inch, wherein the mean cross-sectional area of said bellows is substantially 0.005 square inches, means for placing said bellows in communication with said pressure in the body so that said pressure will cause said bellows to expand and contract linearly as a function of said body pressure substantially 24.5 to 45.5 mils, and means contained within said housing and associated with said bellows for communicating the linear movement of said bellows to a receiver means located external to said body to provide data indicative of said pressure.

2. A pressure sensor apparatus, as claimed in claim 1, wherein said bellows has 41 convolutions and a pitch of substantially 0.010 inch.

3. A pressure sensor apparatus, as claimed in claim 1, wherein the outside diameter of said bellows is substantially 0.100 inch and the inside diameter is substantially 0.060 inch.

4. A pressure sensor apparatus, as claimed in claim 1, wherein said bellows is adapted to expand and contract substantially 35 mils.

5. A pressure sensor apparatus, as claimed in claim 1, wherein said average spring rate is substantially 0.186 pounds per inch.

6. A pressure sensor apparatus for indicating pressure in the body comprising a housing, a bellows contained within said housing, said bellows being resilient and made of gold-plated nickel having essentially 100% memory of position, said bellows further having a plurality of convolutions along its entire length, and a length of substantially 0.410 inch, an average spring rate of approximately 0.130 to 0.242 pounds per inch and a wall thickness substantially within the range of 0.00025 to 0.00033 inch, means for placing said bellows in communication with said pressure in the body so that said pressure will cause said bellows to move linearly as a function of said pressure approximately 24.5 to 45.5 mils, and output means contained within said housing and associated with said bellows for producing an output which is a function of the linear movement of said bellows to a receiver means located external to said body to provide data indicative of said pressure.

7. A pressure sensor apparatus for indicating pressure in the body comprising a housing, a resilient gold-plated nickel bellows contained within said housing having a plurality of convolutions and a length over the convoluted portion of substantially 0.410 inch, said bellows having a wall thickness substantially within the range of 0.00025 to 0.00033 inch, and an average spring rate of approximately 0.130 to 0.242 pounds per inch, means for placing said bellows in communication with said pressure in the body so that said pressure will cause said bellows to contract and expand a distance of approximately 24.5 to 45.5 mils, output means contained within said housing for producing an output which is a function of said pressure, said output means having at least two components, the first of said two components being operatively connected to said bellows and movable therewith when said bellows expands and contracts, the second of said two components being operatively associated with said first component but not movable with said bellows so that when said first component moves the output of said output means varies as a function of said pressure, the output of said output means being adapted to being sensed by a sensor means located external to said body and which is responsive to said output to provide data indicative of said pressure.

8. A pressure sensor apparatus, as claimed in claim 7, wherein said bellows has 41 convolutions and a pitch of substantially 0.010 inch.

9. A pressure sensor apparatus, as claimed in claim 7, wherein said bellows is adapted to expand and contract substantially 35 mils.

10. A pressure sensor apparatus, as claimed in claim 7, wherein the outside diameter of said bellows is substantially 0.100 inch and the inside diameter is substantially 0.060 inch.

11. A pressure sensor apparatus, as claimed in claim 7, wherein said spring rate is substantially 0.186 pounds per inch.

12. A pressure sensor apparatus, as claimed in claim 7, wherein said first component comprises a radioactive source, and said second component comprises a shield means connected to said housing for shielding said radioactive source.

13. A pressure sensor apparatus for indicating pressure in the body comprising a housing, a gold-plated nickel bellows contained within said housing, said bellows substantially cylindrical in shape and having a plurality of convolutions and a length over the convoluted portion of substantially 0.410 inch in its at-rest condition, and having a wall thickness substantially within the range of 0.00025 to 0.00033 inch, and an average spring rate of substantially 0.130 to 0.242 pounds per inch, flexible means associated with said housing and adapted to move as a function of the pressure in said body, a pressure-transmitting fluid contained within said housing and communicating with said flexible means so that said pressure acting upon said flexible means will cause said bellows to contract and expand as a function of said pressure a distance of approximately 24.5 to 45.5 mils, output means contained within said housing having first and second components cooperating to produce an output, said first component being operatively associated with said bellows and movable therewith and said second component being operatively associated with said first component but not movable with said bellows so that said output produced by said output means is a function of the contraction and expansion of said bellows, and ambient pressure sensing means associated with said bellows for compensating for ambient pressure variations acting upon said flexible means whereby said output is sensed by a sensor means located external to said body to provide data indicative of said pressure.

14. A pressor sensor apparatus, as claimed in claim 13, wherein said bellows has 41 convolutions and a pitch of substantially 0.010 inch.

15. A pressure sensor apparatus, as claimed in claim 13, wherein the outside diameter of said bellows is substantially 0.100 inch and the inside diameter is substantially 0.060 inch.

16. A pressure sensor apparatus, as claimed in claim 13, wherein said spring rate is substantially 0.186 pounds per inch.

17. A pressure sensor apparatus, as claimed in claim 13, wherein said first component comprises a radioactive source, and said second component comprises a shield means connected to said housing for shielding said radioactive source.

18. A pressure sensor apparatus for indicating pressure in the human body, particularly intracranial pressure, comprising a housing, bellows means supported within said housing, wherein said bellows means defines a first chamber and a second chamber within said housing, a fluid filled within said first and second chambers, means for placing said first chamber in communication with said pressure to be sensed so that said pressure will cause said bellows means to contract and expand, communication means contained within said housing for communicating the contraction and expansion movement of said bellows means, said communication means having at least two components, the first of said two components being operatively connected to said bellows means and movable therewith when said bellows means expands and contracts, the second of said two components positioned within said first chamber and being operatively associated with said first component but not movable with said bellows means so that the relative movement of said first component with respect to said second component varies as a function of said pressure, said communication means being adapted to being sensed by a sensor means located at a remote position from said housing and free of any physical interconnection with said housing for sensing the relative position of said first and second components to provide data indicative of said pressure, wherein said bellows means comprises a gold-plated nickel bellows having a plurality of convolutions and a length over the convoluted portion of substantially 0.410 inch, a wall thickness substantially within the range of 0.00025 to 0.00033 inch, and an average spring rate of substantially 0.130 to 0.242 pounds per inch, wherein the bellows is substantially cylindrically shaped and has a mean cross-sectional area of substantially 0.005 square inches, and wherein said bellows is adapted to contract and expand a distance of approximately 24.5 to 45.5 mils when exposed to intracranial pressure.

* * * * *